United States Patent [19]
Erickson

[11] Patent Number: 5,610,307
[45] Date of Patent: Mar. 11, 1997

[54] DIRECT ISOLATION OF OPTICALLY PURE (3S)-1,2,3,4-TETRAHYDROISOQUINOLINE-3-CARBOXYLIC ACID

[75] Inventor: Robert A. Erickson, DesPlaines, Ill.

[73] Assignee: The Nutra Sweet Company, Deerfield, Ill.

[21] Appl. No.: 404,478

[22] Filed: Mar. 14, 1995

[51] Int. Cl.⁶ .................................................. C07D 217/02
[52] U.S. Cl. ......................................................... 546/147
[58] Field of Search ............................................... 546/147

[56] References Cited

PUBLICATIONS

Hayashi et al, *Chemical & Pharmaceutical Bulletin*, vol. 31, No. 1, Jan. 1983, pp. 312–314.
O'Reilly et al, *Synthesis*, No. 7, Jul. 1990, pp. 550–556.
Shiraiwa et al, *Bull. Chem. Soc. Jpn.* vol. 64, No. 12, 1991, pp. 3729–3731.

*Primary Examiner*—Zinna Northington Davis

[57] ABSTRACT

A substantially pure L-isomer of (3S) 1,2,3,4-tetrahydroisoquinoline is produced from an optically enriched mixture by cyclizing D- or L-phenylalanine using a solution of formaldehyde and hydrochloric acid, adjusting the pH of the mixture to yield the neutral free acid form and treating the mixture with dilute acetic acid of from about 5.0 wt/wt % to about 25 wt/wt %. The mixture is then refluxed at 80° C. to 95° C. and cooled to about 10° C. to yield amorphous powdery solid material.

6 Claims, No Drawings

DIRECT ISOLATION OF OPTICALLY PURE (3S)-1,2,3,4-TETRAHYDROISOQUINOLINE-3-CARBOXYLIC ACID

FIELD OF THE INVENTION

The present invention relates generally to an improved method for the resolution of a racemic mixture of isomeric forms of a compound into its substantially optically pure form. More specifically, the method relates to the stereospecific isolation of an optically pure amino acid in a single step.

BACKGROUND OF THE INVENTION

In the world of drug design, the key to activity is making a drug that will react on a cellular level at a specific site. One of the best ways to accomplish this is to synthesize a chiral ("handed") molecule that is site specific for a given receptor and has activity that blocks, inhibits or alters the normal chemistry at that site. In AIDS and cancer research for example, many active compounds that may prove valuable in eventually providing a cure have been found to be chiral. This chiral nature refers to the fact that the compound may exist as two asymmetric molecules that are mirror images of one another, i.e., they are related optically like right (D) and left (L) hands, hence the term "handed". However, since chemical reactions involving even pure (one isomer) chiral starting materials can yield mixtures of isomers (racemates), it is important to be able to isolate the desired chiral compound in its pure form since only one isomer will likely be active. This can be done in a variety of ways on a lab scale (crystallizations, chromatography, synthetic transformations, complexes), but most of these are not practical on a manufacturing scale.

Amino acids and peptides serve as important pharmaceutical and food additives in both human and animal diets and their production and purification have become vital to numerous food, drug and chemical industries. Many amino acids are made either chemically or through fermentation processes which require the separation and isolation of the desired amino acids from the broth.

Many amino acids exist as two optically active enantiomers, the L (levorotary) and D (dextrorotary) isomers. Most applications require the separation of the two from their racemic mixture that is produced during chemical manufacture. L-phenylalanine for example, is a precursor or component for many pharmaceutically active peptides and food additives and it exists in both the L and D forms. In many cases, the L form of the compound may be active whereas the D-isomer is not and visa versa. However, the synthesis of the amino acid or peptide in question produces a racemic mixture of both and hence it would be advantageous to find a way to isolate only the active isomer.

Various methods for separating the L and D isomers are known and generically are referred to as resolution. The most common method of resolving D,L-mixtures involves treating them with an optically active compound known as a resolving agent, followed by fractional crystallization of the resulting mixture of compounds (diastereroisomers) in solution. For practical resolution, it is necessary to find a combination of resolving agent and solvent which will give good crystallization behavior together with a pronounced difference in solubility between the diastereoisomers. Examples of this technique as applied to the resolution of an amino acid are described in U.S. Pat. No. 2,556,907 to Emmick and U.S. Pat. No. 2,657,230 to Rogers. These patents discuss methods to resolve D,L-lysine in which optically active glutamic acid is employed as the resolving agent.

More recently, phenylalanine has been resolved by the enzymatic hydrolysis of its racemic esters. The enzyme, chymotrypsin, selectively hydrolyzes L-phenylalanine esters. Hence, L-phenylalanine is recovered from a mixture of the D,L-phenylalanine ester. An example of this process is European Patent Appln. EP 174,862 to Empie Aug. 17, 1984.

The isoquinoline derivative (3S)-1,2,3,4-tetrahydroisoquinoline-3-carboxylic acid (L-TIC-A) is an amino acid that has shown to be a useful starting material in the enzymatic and chemical synthesis of a number of pharmaceutically active peptides and peptide analogues such as the bradykinin agonists, ACE inhibitors and hypotensive drugs. The D-form of the isomer is not as useful, however, as this isomer is relatively inactive. This presents a problem in that the synthesis of the compound from phenylalanine using the Pictet-Spengler reaction results in a mixture of both isomers. A method for the preparation of optically pure (3S)-1,2,3,4-tetrahydroisoquinoline-3-carboxylic acid is therefore desirable.

In the Pictet-Spengler reaction, chiral (L) phenylalanine is reacted as set forth below to produce a major product, (L) TIC-A (85–90%) and a minor product, (D) TIC-A (15–10%). See Pictet, A; Spengler, T. Ber Dtsch Chem Ges 1911,44, 2030; and Archer, S. J Org. Chem 1951, 16, 430. The reaction occurs as follows.

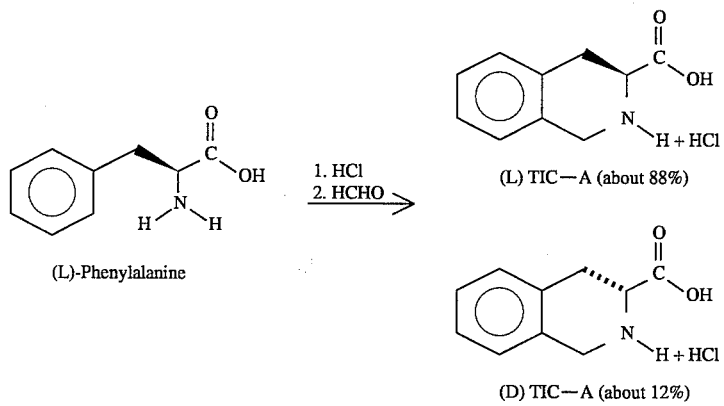

This mixture of D,L TIC-A•HCl, must be neutralized and purified to isolate only (L) TIC-A, free acid, which is the "key" intermediate in the synthesis of the chiral product (L) N-t-Butyl-1,2,3,4-tetrahydro-3-isoquinoline carboxyamide (L-TIC-C) and ultimately (L) N-t-Butyl-decahydro-3-isoquinoline carboxamide (L-TIC-D) which are compounds useful as starting materials in the synthesis of a number of pharmaceutically active drugs. For example, N'-[1(S)benzyl-3-[4a(S),8a(S)-3-(S)-(tertbutylcarbamoyl)decahydroisoquinoline-2-yl]-2(R)-hydroxypropyl]-N"-(quinolin-2-ylcarbonyl)-L-asparaginamide (Roche) is one derivative useful as an anti-viral and anti-HIV agent. Another compound, 3-Isoquinoline carboxylic acid, 2-[2-[(1-carboxy-3-phenylpropyl (amino]-1-oxopropyl]1,2,3,4-tetrahydro-[3-S [2R(R),3R]-[CAS] (Parke Davis) is therapeutically useful as an antihypertensive. The purity of (L) TIC-A is crucial because none of the later intermediates can be practically purified at the manufacturing level if there is a racemic mixture consisting of the two L- and D-isomers.

Racemic and optically pure 1,2,3,4-tetrahydroisoquinoline-3-carboxylic acids and esters have also been prepared by the base-catalyzed cyclization reaction of 1,2-bis(halomethyl)benzenes with dimethyl 2-(acetylamino) malonate with subsequent decarboxylation and amide cleavage. Kammermaier et. al. Synthesis 1157 (November 1992) Enantiomer resolution is achieved by esterification with menthol followed by column chromatography or by distereomeric salt separation of the benzylic ester with mandelic acid and a base catalyzed saponification.

Shiraiwa et. al., Bull. Chem. Soc. Jpn. 64 3729 (December 1991) reports the asymmetric transformation of L-TIC-A through the use of (1S)-10-camphor-sulfonic acid as a resolving agent that yields a salt of L-TIC-A with 90% optical purity. The TIC obtained from the salt was purified to give a yield of optically pure L-TIC-A of about 80%.

EPA 496 369 to Kammermaier discloses a method for the preparation of racemic TIC-A whereby dihalo-o-xylene is cyclized with N-acylamidomalonic acid dialkyl esters in a basic medium to dicarboxylic esters which are subsequently saponified and acidified to the final product.

EPA 049 658 to Remond et. al. discloses the preparation of (3S)-tetrahydroisoquinoline-3-carboxylic acid through the treatment of (S)β-phenylalanine with concentrated hydrochloric acid and a 40% formaldehyde solution. After heating and subsequently cooling, the compound in its racemic forms crystallizes out.

U.S. Pat. No. 4,847,409 to Kidman et. al. discloses a method for the isolation of a substantially pure L-isomer of an amino acid from its D,L-mixture that does not require the use of a resolving agent, the formation of a derivative of the amino acid or additional enzymatic reactions. The method is based on the equal saturation point whereby the L-isomer can be precipitated out and separated from the D-isomer when the relative concentration of the D-isomer is less than 7.0%.

As mentioned earlier, several basic ways of purifying these and other isomers are known: crystallization (often several are necessary to give a pure isomer); chromatography; synthetic transformation whereby the compound mixture is first converted into one that is more easily purified, it is purified and the purified material is returned to its original form; or complexation of the desired isomer is carried out with a resolving reagent that yields a more easily separated mixture, with subsequent removal of the resolving agent. All of these methods will work, but at a price, either higher synthetic costs and/or lower overall yields. Moreover, few if any at all are feasible for a large scale manufacturing process.

Crystallization of the racemic mixture is relatively straight forward on the laboratory scale (see the Journal of Medicinal Chemistry, 1988, Vol. 31, No. 11, 2095–2096), but several crystallizations are usually required and this method is not feasible on a manufacturing scale. Synthetic transformation from the "acid" form to the "ester salt" form is another purification technique (Chem. Pharm. Bull., 31,313–14, 1983) which requires synthesis of the ester salt followed by fractional crystallization and subsequent de-esterification. This invariably results in extra expense in time/labor/materials necessary to obtain a pure product. Asymmetric transformation of racemic mixtures by use of a resolving agent (Bull. Chem Soc. Jpn. 64, 3729–31, 1991) requires a specific resolving agent which must be reacted with the mixture and later removed from the pure isomer, which again, results in extra expense. Chromatography is an excellent separation method that is an essential small, lab-scale tool but which seldom can be utilized for purification of isomers on a large manufacturing scale.

In all of these conventional prior art methods, additional steps involving the use of a resolving agent in a chemical or enzymatic reaction or some combination of these is required to form derivatives of L-TIC-A in order to isolate the desired isomer. The present invention permits the separation of an optically pure L-isomer from the D,L-mixture and in the same step, purifies it from other amino acids, salts, etc. which are manufacturing contaminants, without the requirement of a resolving agent, without the subsequent formation of a derivative of the amino acid in question and without enzymatic reaction. There is also no need as is found in the methods known in the art of first converting the free acid to the ester, purifying it and then reconverting the ester to the optically pure free acid. These additional steps and intermediates are thereby done away with resulting in a more economically efficient, cleaner product.

SUMMARY OF THE INVENTION

An improved method for the isolation of optically pure (3S)-1,2,3,4-tetrahydroisoquinoline-3-carboxylic acid comprises preparing optically enriched mixture from L-phenylalanine via the Pictet-Spengler reaction and treating that racemized mixture with acetic acid at reflux. The solution is cooled to precipitate the optically pure isomer which is then filtered, washed and dried.

DETAILED DESCRIPTION OF THE INVENTION

The present invention pertains to a "one-pot" method for the preparation of an optically pure (3S)-1,2, 3,4-tetrahydroisoquinoline-3-carboxylic acid (L-TIC-A) that does away with the multi-step processes of the prior art which generally require conversion of the free acid forms of the L- and D-isomers to the ester which is then purified and reconverted back to the optically pure free acid.

The following is an overview of the chemistry that yields the pure L-TIC-A:

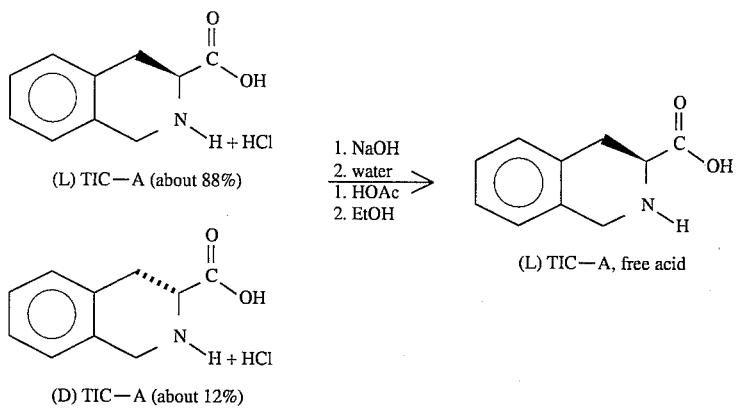

This simple purification and isolation process for isomerically pure L-TIC-A is a practical means of purifying this "key" intermediate on a manufacturing scale and thus surprisingly and unexpectedly provides a viable supply of starting material for the synthesis of L-TIC-C and L-TIC-D. This process should also purify a racemic mixture of isomers formed from (D) phenylalanine to give pure D-TIC-A, free acid by similar analogy.

Without being bound to any theory, the process works essentially by changing the solubility of the minor isomer, so it goes into solution, while the bulk of the major isomer remains undissolved and is then easily separated from the minor isomer by filtration or centrifugation. The solid product is then washed and ready for use in the next synthetic step.

As discussed previously, racemic phenylalanine is mixed with formaldehyde in a cyclocondensation reaction in the presence of concentrated hydrochloric acid. The solution is recrystallized using highly diluted solutions of ethanol in water and the crystals recovered and dried. This method, known as the Pictet-Spengler reaction, produces a racemized reaction product comprised of approximately equal quantities of the D- and L-isomers of TIC-A. Even when enantiomerically pure phenylalanine is used as a substrate for the reaction, some racemization takes place requiring further treatment if an isomerically pure compound is to be obtained.

The racemic mixture consists essentially of two forms of the free acid of TIC-A. The optically enriched mixture which consists of powdery solids (~12% D, ~88% L) is then contacted with a solution of glacial acetic acid diluted with water and/or water and alcohol. The concentration of the glacial acetic acid may range from about 5.0 wt/wt % to about 25.0 wt/wt % and preferably from about 10.0 wt/wt % to about 16.0 wt/wt %. The concentration of the alcohol may range from 0 wt/wt % to about 20.0 wt/wt % and preferably for about 5.0 wt/wt % to about 10.0 wt/wt %. The current alcohol of choice is ethyl alcohol. The amount of TIC-A treated can vary depending on the degree of enrichment of the major isomer in the mixture.

The mixture is refluxed for approximately 0.1–6.0 hours, preferably for 2.0 to about 4.0 hours, then cooled to about 10° C. to about 15° C. to yield isomerically pure L-TIC-A. The solids are then filtered, washed with ethyl alcohol and dried using standard chemical manufacturing procedures.

The following examples are given in order to more fully describe the aspects of the present claimed invention. They are for illustrative purposes only and it is understood that minor changes may be made with respect to the amounts and/or volumes of reagents, the reagents themselves and the reaction parameters such as temperature, pressure and time which may alter the results somewhat. It is to be recognized that any such changes that do not significantly add to or vary the procedure and/or the isolated compounds produced are still considered as falling within the spirit and scope of the present invention as defined by the claims that follow.

EXAMPLE 1

One (1.0) gram of an optically enriched mixture of the free-acid form of TIC-A was contacted with a solution comprised of 4.14 grams of glacial acetic acid and 50.0 grams of water in a 100 ml. flask. The mixture was stirred and heated to reflux, then held at reflux for 6 minutes (all solids dissolved). The solution was cooled while stirring overnight to approximately 25° C.; solids precipitated.

The purified L-TIC-A solids were filtered and washed two times with 5 ml. water and two times 5 ml. acetone. The isolated solids were air-dried briefly, then were dried overnight in vacuum oven at approximately 50° C. The dried product yielded 0.506 grams of the white solid powder.

The compound's optical rotation was determined at 25° C. (after dissolution in a 1.4N sodium hydroxide solution) using the following equation:

$$[\alpha]_D^T = \frac{(100)(\alpha^1)}{(b)(c)}$$

where

T=temperature of cell

D=sodium light source $\alpha^1$=observed rotation (in degrees)

b=cell length in decimeters c=concentration of solution

The optical rotation of a 0.180 gram sample of the product in 1.4N sodium hydroxide to 10 ml. volume (volumetric flask) was −168.3°. References in the literature report optical rotation values of −177.4° to −167.0° for the L-isomer of TIC-A and +176.8° to +167.0° for the D-isomer. Commercially available L-TIC-A gave a rotation at 25° that was −162.6° while commercially available D-TIC-A gave a rotation at 25° that was +165.0°.

EXAMPLE 2

Twenty-five (25.0) grams of an optically enriched mixture of the free-acid form of TIC-A were contacted with a solution comprised of 75.0 grams of glacial acetic acid, 40.0 grams of ethyl alcohol and 375.0 grams of water in a 1.0 liter Morton flask. The mixture was stirred and heated to reflux, then held at reflux for about 1.5 hours. The mixture was then cooled to approximately 25° C.

The purified L-TIC-A solids were filtered and washed two times with 100 ml. of water and two times with 100 ml. of acetone. The resultant product was dried overnight in a vacuum oven at approximately 50° C.

The dry product yielded 19.07 grams of white solid powder. The optical rotation at 25° was −167.2°

EXAMPLE 3

Forty (40.) grams of a crude (dry) optically enriched mixture of the hydrochloric acid form of TIC-A were contacted with a solution comprised of 26 grams of ethyl alcohol and 285 grams of water in a 1.0 liter Morton flask. While vigorously stirring the mixture, 10 N sodium hydroxide was added to adjust the pH to 4.5 to 6.0.

Next, 75.0 grams of ethyl alcohol and 169.0 grams of glacial acetic acid were added to the thick slurry. The mixture was heated to 88° C. to 90° C. and stirred at this temperature for two (2) hours. The mixture was cooled in an ice-bath to 10° C. to 15° C. and stirred at this temperature for at least 15 minutes. The purified L-TIC-A was filtered and washed two times with 150 ml. cool water. The 'wet-cake' was dried overnight in a vacuum oven at approximately 50° C.

The dry product yielded 15.07 grams of white powdery solids. Analysis by chiral HPLC (high performance liquid chromatography) showed L-TIC-A was 95.6 wt/wt % and D-TIC-A was not detected.

What I claim is:

1. A method for the isolation of a substantially pure isomer of (3S)-1,2,3,4-tetrahydroisoquinoline-3-carboxylic acid comprising:

a. preparing a crude optically enriched mixture of said isoquinoline derivative through the cyclization of D- or L-phenylalanine in the presence of formaldehyde and hydrochloric acid;

b. adjusting the pH to yield the neutral free acid form;

c. treating said mixture with a dilute acetic acid solution;

d. heating said mixture at increased temperature; and e. cooling said mixture so as to yield said amino acid powder as a single, isolated isomer.

2. The method of claim 1 wherein said racemic mixture comprises the D- or L- forms of said (3S) 1,2,3, 4-tetrahydroisoquinoline-3-carboxylic acid.

3. The method of claim 2 wherein said mixture is treated with dilute acetic acid at a concentration of from about 5.0 wt/wt % to about 25 wt/wt %.

4. The method of claim 3 wherein said concentration of acetic acid ranges from about 10 wt/wt % to about 16 wt/wt %.

5. The method of claim 4 wherein said dilute acetic acid solution further comprises ethyl alcohol.

6. The method of claim 5 wherein said mixture is heated at a temperature of from about 80° C. to about 95° C.

* * * * *